(12) United States Patent
Prakash et al.

(10) Patent No.: US 7,087,789 B2
(45) Date of Patent: Aug. 8, 2006

(54) METHODS FOR NUCLEOPHILIC FLUOROMETHYLATION

(75) Inventors: G. K. Surya Prakash, Hacienda Heights, CA (US); Jinbo Hu, Los Angeles, CA (US); George A. Olah, Beverly Hills, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 10/755,902

(22) Filed: Jan. 12, 2004

(65) Prior Publication Data

US 2004/0230079 A1 Nov. 18, 2004

Related U.S. Application Data

(60) Provisional application No. 60/440,011, filed on Jan. 13, 2003.

(51) Int. Cl.
*C07C 319/00* (2006.01)
(52) U.S. Cl. .................... 568/56; 568/323; 568/437
(58) Field of Classification Search ............ 568/56, 568/323, 437
See application file for complete search history.

(56) References Cited

U.S. PATENT DOCUMENTS 5,008,425 A  4/1991 Stahly ................. 556/436
5,446,218 A  8/1995 Webster et al. ............. 17/8

FOREIGN PATENT DOCUMENTS

WO    WO 98/22435    * 5/1998
WO    WO 9822435      5/1998

OTHER PUBLICATIONS

Stahly, Nucleophilic Addition of Difluoromethyl Phenyl Sulfone to Aldehydes and Various Transformation of the Resulting Alcohols, Journal of Fluorine Chemistry, 43, 1989, 53-66.*
Russell et al., Effective Nucleophilic Trifluoromethylation with Fluoroform and Common Base, Tetrahedron, 54, 1998, 13771-13782.*
Large et al., Nucleophilic Trifluoromethylation of Carbonyl Compounds and Disulfides with Trifluoromethane and Silicon-Containing Bases with Fluoroform and Common Base, Snythesis, J. Org. Chem., 2000, 65, 8848-8856.*
Prakash, G.K.S.; Krishnamurti, R.; Olah, G.A., J. Am. Chem. Soc. 1989, 111, 393-395.

(Continued)

*Primary Examiner*—Johann Richter
*Assistant Examiner*—Chukwuma Nwaonicha
(74) *Attorney, Agent, or Firm*—Winston & Strawn LLP

(57) ABSTRACT

A novel, convenient and efficient method for trifluoromethylation of substrate compounds is disclosed. Particularly, alkoxide and hydroxide induced nucleophilic trifluoromethylation of carbonyl compounds, disulfides and other electrophiles, using phenyl trifluoromethyl sulfone $PhSO_2CF_3$ (or sulfoxide $PhSOCF_3$) is disclosed. A method of both symmetrical and unsymmetrical anti-2,2-difluoropropan-1,3-diols with high diastereoselectivity (up to 94% de) is disclosed using difluoromethyl phenyl sulfone. This unusual type of high diastereoselectivity was obtained via an intramolecular charge-charge repulsion effect rather than the traditional steric control (based on the Cram's rule). Thus, difluoromethyl phenyl sulfone can be used as a novel difluoromethylene dianion species ("$^-CF2^-$"), which can couple two electrophiles (such as diphenyl disulfide or non-enolizable aldehydes) to give new difluoromethylenated products.

26 Claims, 8 Drawing Sheets

OTHER PUBLICATIONS

Prakash, G.K.S.; Yudin, A.K., Chem. Rev. 1997, 97, 757-786.
Prakash, G.K.S.' Hu, J.; Olah, G.A., J. Org. Chem. 2003, 68, 4457-4463.
Shono, T.; Ishifume, M.; Okada, T.; Kashimura, S., J. Org. Chem. 1991, 56, 2-4.
Barhdadi, R.; Troupel, M.; Perichon, J., Chem. Comm. 1998, 1251-1252.
Folleas, B.; Marek, I.; Normant, J.F.; Saint-Jalmes, L. Tetrahedron Lett. 1998, 39, 2973-2976.
Folleas, B.; Marek, I.; Normant, J.F.; Saint-Jalmes, L. Tetrahedron 200, 56, 275-283.
Russell, J.; Roques, N., Tetrahedron, 1998, 54, 13771-13782.
Large, S.; Roques, N.; Langlois, B.R., J. Org. Chem. 2000, 65, 8848-8856.
Roques, N.; Mispelaere, C., Tetrahedron Lett. 1999, 40, 6411-6414.
Billard, T.B.; Langlois, B.R. Org. Lett. 2000, 2, 2101-2103.
Billard, T.; Langlois B.R.; Blond, G., Eur. J. Org. Chem., 2001, 1467-1471.
Billard, T.; Langlois, B.R., J. Org. Chem., 2002, 67, 997-1000.
Langlois, B.R.; Billard, T., Synthesis, 2003, 185-192.
Ait-Mohand, S.; Takechi, N.; Medebielle, M.; Dolbier, W., Jr., Org. Lett., 2001, 3, 4271-4273.
Motherwell, W.B.; Storey, L.J., Synlett, 2002, 646-648.
Jablonski, L.; Joubert, J.; Billard, T.; Langlois, B.R., Synlett, 2003, 230-232.
Inschauspe, D.; Sortais, J.P.;; Billard, T.; Langlois, B.R., Synlett, 2003, 233-235.
Jablonski, L.; Billard, T.; Langlois, B.R.; Tetrahedron Lett., 2003, 44, 1055-1057.
Shein, S.M.; Krasnopol'skaya, M.I.; Boiko, V.N., Zh. Obshei Khim., 1966, 36, 2141.
Steensma, R.W.; Galabi, S.; Tagat, J.R.; McCombie, S.W., Tetrahedron Lett., 2001, 42, 2281-2282.
Barrera, M.D.; Cheburkov, Y.; Lamanna, W.M., J. Fluorine Chem., 2002, 117, 13-16.
Yudin, A.K.; Prakash, G.K.S.; Deffieux, D.; Bradley, M.; Bau, R.; Olah, G.A., J. Am. Chem. Soc., 1997, 119, 1572-1581.
Kuroboshi, M.; Ishihara, T.; Bull. Chem. Soc. Jpn., 1990, 63, 1185-1190.
Hine, J.; Porter, J.J., J. Am. chem. Soc., 1960, 82, 6178-6181.
Stahly, P., J. Fluorine Chem., 1989, 43, 53-66.
Saikia et al., "Chemistry of Trichiorofluoromethane: Synthesis of Chiorofluoromethyl Phenyl Sulfone and Fluoromethyl Ohenyl Sulfone and Some of Their Reactions", Journal of Organic Chemistry, vol. 66 (3), pp. 643-647 (2001).

* cited by examiner (R = H, alkyl group. E, E' = electrophiles, such as disulfides, aldehydes)

9

10

Stepwise formation of 12 and 13.

[a] $^{19}$F NMR for *anti* isomer: -120.9 ppm (pseudo t, $^3J_{F-H}$ = 11.4 Hz, 2F).
[b] $^{19}$F NMR: -104.4 ppm (dd, $J$ = 238.0 Hz, 2.8 Hz, 1F);
    -119.8 ppm (dd, $J$ = 238.0 Hz, 21.0 Hz, 1F).

METHODS FOR NUCLEOPHILIC FLUOROMETHYLATION

This application claims the benefit of provisional application Ser. No. 60/440,011, filed on Jan. 13, 2003, the entirety of which is incorporated herein by reference thereto.

TECHNICAL FIELD

This invention relates to a novel synthetic method for the nucleophilic trifluoromethylation and difluoromethylenation of substrate compounds. The invention more particularly relates to the alkoxide and hydroxide induced trifluoromethylation and difluoromethylenation of substrates using tri- and difluoromethyl sulfones and sulfoxides.

BACKGROUND ART

In the past two decades, organofluorine compounds have attracted much attention due to their unique properties and unusual reactivities. Among them, trifluoromethyl group ($CF_3$) containing compounds are of particular importance for different applications in the materials field, as well as in the pharmaceutical and agrochemical industries. Although many trifluoromethylation methods are known, such as organometallic, nucleophilic, electrophilic and radical trifluoromethylations, fluoride induced nucleophilic trifluoromethylation with (trifluoromethyl)trimethylsilane (TMS-$CF_3$) previously developed by the present inventors is considered a straightforward, convenient and versatile method. See, Prakash, G. K. S.; Krishnamurti, R.; Olah, G. A. *J. Am. Chem. Soc.* 1989, 111, 393; Prakash, G. K. S.; Yudin, A. K. *Chem. Rev.* 1997, 97, 757, the content of which is incorporated herein by reference thereto. TMS-$CF_3$ was commonly prepared from ozone-depleting trifluoromethyl halides, but recently, a non-Freon based preparation has been reported. See Prakash, G. K. S.; Hu, J.; Olah, G. A., *J. Org. Chem.* 2003, 68, 4457, incorporated herein by reference thereto.

Since the 1990s, there has been increasing research interest in trifluoromethylation using trifluoromethane ($CF_3H$) as a trifluoromethylating precursor. $CF_3H$ has low toxicity and is not ozone-depleting. It is a side-product of the multi-step industrial synthesis of Teflon.® The efficient production of $CF_3H$ has been disclosed via fluorination of methane with hydrogen fluoride and chlorine (Webster J. L.; Lerou, J. J. U.S. Pat. No. 5,446,218, 1995). For example, Shono and co-workers used electrochemically reduced 2-pyrrolidone base to deprotonate $CF_3H$ to generate the trifluoromethyl anion equivalent that reacts with aldehydes and ketones (Shono, T.; Ishifume, M.; Okada, T.; Kashimura, S. *J. Org. Chem.* 1991, 56, 2). Troupel et al. also reported that cathodic reduction of iodobenzene generates a strong base, which deprotonates $CF_3H$, inducing its addition to aldehydes (Barhdadi, R.; Troupel, M.; Perichon, J. *Chem. Comm.* 1998, 1251). Thereafter, two research groups carried out extensive studies on the nucleophilic trifluoromethylation using $CF_3H$ as a precursor. Normant and co-workers have demonstrated the trifluoromethylation of aldehydes by $CF_3H$/potassium dimsylate in DMF (Folleas, B.; Marek, I.; Normant, J.-F.; Saint-Jalmes, L. *Tetrahedron Lett.* 1998, 39, 2973; Folleas, B.; Marek, I.; Normant, J.-F.; Saint-Jalmes, L. *Tetrahedron* 2000, 56, 275). They suggested that the $CF_3^-$/DMF adduct was the key intermediate in the trifluoromethyl transfer process.

Additionally, Roques, Langlois and co-workers reported the nucleophilic trifluoromethylation of carbonyl compounds and disulfides with $CF_3H$ and different bases in DMF. See, (a) Russell, J.; Roques, N. *Tetrahedron* 1998, 54, 13771. (b) Large, S.; Roques, N.; Langlois, B. R *J. Org. Chem.* 2000, 65, 8848. (c) Roques, N.; Russell, J.; Langlois, B.; Saint-Jalmes, L.; Large, S. *PCT Int. Appl.* 1998, WO 9822435. (d) Roques, N.; Mispelaere, C. *Tetrahedron Lett.* 1999, 40, 6411, each of which are incorporated herein by reference.

$CF_3^-$/N-formylmorpholine adduct was also developed as a stable reagent for the trifluoromethylation of non-enolizable carbonyl compounds (Billard, T. B.; Langlois, B. R. *Org. Lett.* 2000, 2, 2101). Under similar consideration, piperazino hemiaminal of trifluoro-acetaldehyde was also used as a trifluoromethylating agent (Billard, T.; Langlois, B. R.; Blond, G. *Eur. J. Org. Chem.* 2001, 1467; Billard, T.; Langlois, B. R. *J. Org. Chem.* 2002, 67, 997; Langlois, B. R.; Billard, T. *Synthesis* 2003, 185).

Trifluoromethyl iodide ($CF_3I$) has also been successfully used as a nucleophilic trifluoromethylating agent under the activation of electron-donating tetrakis-(dimethylamino)ethylene (TDAE) (Ait-Mohand, S.; Takechi, N.; Medebielle, M.; Dolbier, W. Jr. *Org. Lett.* 2001, 3, 4271). Motherwell et al. reported the nucleophilic trifluoromethylation using trifluoromethyl-acetophenone-N,N-dimethyl-trimethylsilylamine adduct (Motherwell, W. B.; Storey, L. J. *Synlett* 2002, 646). Langlois et al. also have reported nucleophilic trifluoromethylations of non-enolizable carbonyl compounds using trifluoroacetic acid derivatives, trifluoromethanesulfinic acid derivatives and trifluoroacetophenone ((a) Langlois, B. R.; Billard, T. *Synthesis* 2003, 185. (b) Jablonski, L.; Joubert, J.; Billard, T.; Langlois, B. R. *Synlett* 2003, 230. (c) Inschauspe, D.; Sortais, J.-P.; Billard, T.; Langlois, B. R. *Synlett* 2003, 233. (d) Jablonski, L.; Billard, T.; Langlois, B. R. *Tetrahedron Lett.* 2003, 44, 1055). More recently, a nucleophilic trifluoromethylation method using trifluoroactetamides from amino alcohols was reported (Joubert, J.; Roussel, S.; Christophe, C.; Billard, T.; Langlois, B. R.; Vidal, T. *Angew. Chem. Int. Ed.* 2003, 42, 3133). Thus, there is a need to develop a convenient and non-ozone depleting reagent for the nucleophilic trifluoromethylation.

Nucleophilic displacement of the trifluoromethyl group has been reported for trifluoromethyl aryl sulfones with sodium methoxide (Shein, S. M.; Krasnopol'skaya, M. I.; Boiko, V. N., *Zh. Obshei Khim.* 1966, 36, 2141). A similar reaction between trifluoromethyl aryl sulfone and Grignard reagents has been reported for the preparation of sulfones (Steensma, R. W.; Galabi, S.; Tagat, J. R.; McCombie, S. W., *Tetrahedron Lett.* 2001, 42, 2281). More recently, Cheburkov et al. reported that perfluoroalkyl sulfones react with metal hydroxides in water or alcohol solution and with ammonia to form fluorinated sulfonic acid derivatives (Barrera, M. D.; Cheburkov, Y.; Lamanna, W. M. *J. Fluorine Chem.* 2002, 117, 13).

A reductive trifluoromethylation using trifluoromethyl sulfides, sulfoxides and sulfones as trifluoromethyl ($CF_3$) group precursors has previously been reported (Prakash, G. K. S.; Hu, J.; Olah, G. A., *J. Org. Chem.* 2003, 68, 4457). Under reductive conditions when magnesium metal was used, however, the reaction only worked with chlorosilanes as electrophiles, while attempts to react with carbonyl compounds failed.

All of these methods of trifluoromethylation or difluoromethylation have drawbacks. First of all, trifluoromethane is a low-boiling gas (b.p. −84° C.) and its handling as a reagent in the laboratory is not convenient. Second, none of these trifluoromethylations work well with enolizable carbonyl compounds. Thus, there remains a need for a convenient and efficient method for the nucleophilic trifluoromethylation.

Furthermore, due to the unique properties of fluorine atom, more and more organofluorine compounds have been found to have certain biological effects that mimic or block other compounds or that provide polar or lipophilic effects. For instance, C—F bond is known to mimic a C—H bond because of its similar bond length, and difluoromethylene group is known to be isosteric and isopolar to an ethereal oxygen (Yudin, A. K.; Prakash, G. K. S.; Deffieux, D.; Bradley, M.; Bau, R.; Olah, G. A. *J. Am. Chem. Soc.* 1997, 119, 1572–1581; and the references therein). Thus, the synthesis of fluorine-containing analogs of bioactive natural products are of great interest for their potential applications in pharmaceutical industry. Since anti-1,3-diol functionality is a fundamental unit in many naturally occurring compounds, its stereoselective preparation is always attractive to synthetic organic chemists. anti-2,2-Difluoropropan-1,3-diols 3 are a group of interesting compounds, however, not much is known about their synthesis. Currently, the only reported method to synthesize these compounds is via the diasteroselective Meerwein-Pondorff-Verley reduction of α,α-difluoro-β-hydroxy ketones (Kuroboshi, M.; Ishihara, T. *Bull. Chem. Soc. Jpn.* 1990, 63, 1185–1190). The disadvantage of this approach is the requirement of preparation of α,α-difluoro-β-hydroxy ketones as the precursors. In 1997, the preparation of difluorobis(trimethylsilyl)methane (TMSCF$_2$TMS) as a potential difluoromethylene dianion ("$^-$CF$_2^-$") equivalent was reported (Yudin, A. K.; Prakash, G. K. S.; Deffieux, D.; Bradley, M.; Bau, R.; Olah, G. A. *J. Am. Chem. Soc.* 1997, 119, 1572–1581), but TMSCF$_2$TMS was found only to couple with one molecule of aldehyde such as benzaldehyde to give 2,2-difluoro-1-phenylethanol (after acidic hydrolysis). Thus, there remains a need to develop a synthetic methodology for difluoromethylenation to introduce difluoromethylene dianion species ("$^-$CF$_2^-$") to prepare 2,2-difluoropropan-1,3-diols directly from the carbonyl compounds.

SUMMARY OF THE INVENTION

With these considerations in mind, a long sought after, yet simple and efficient method for the nucleophilic trifluoromethylation and difluoromethylenation of fluoromethylatable substrates has been developed. In addition, a convenient method of preparing 2,2-difluoropropan-diols directly from carbonyl compounds has also been developed.

One aspect of the invention provides a convenient method for preparing trifluoromethylated substrates by reacting a substrate, a trifluoromethylating agent, and an alkoxide or a hydroxide base, under reaction conditions sufficient to trifluoromethylate the substrate. The reaction conditions include a temperature between about −25° C. to about 55° C., and for a time of between 30 minutes to 20 hours, and preferably include a temperature of between −30° C. to about room temperature.

In accordance with the method of the invention, the trifluoromethylating agent includes but is not limited to trifluoromethyl phenyl sulfone, trifluoromethyl phenyl sulfoxide, and methyl trifluoromethyl sulfone. The alkoxide or hydroxide base includes but is not limited to potassium tert-butoxide, sodium methoxide, and potassium hydroxide.

In a preferred embodiment of the invention, the alkoxide or hydroxide base is added to a mixture including the substrate and the trifluoromethylating agent. The reaction mixture is stirred at a first temperature, and is then warmed to a second temperature. Preferably, the mixture is warmed for about 2 hours.

Another aspect of the invention provides a method for preparing a difluoromethylenated substrate by reacting a substrate with a difluoromethylenating agent and an alkoxide or hydroxide base under conditions sufficient to difluoromethylenate the substrate. In accordance with the invention, the difluoromethylating agent includes but is not limited to difluoromethyl phenyl sulfone or difluoromethyl sulfoxide. The alkoxide or hydroxide base includes but is not limited to potassium tert-butoxide, sodium methoxide, and potassium hydroxide.

Preferably, the trifluoromethylation and the difluoromethylenation reactions take place in the presence of a solvent, for example, DMF or DMSO.

In accordance with the invention, a 2,2-difluoro-propan-1,3-diol may be prepared by these methods. A difluorodisulfide having the general formula RSCF$_2$SR, wherein R is an aryl or an alkyl group may also be prepared in this manner.

It is to be understood that both the foregoing general description and the following detailed description are exemplary and are intended to provide further explanation of the invention claimed.

BRIEF DESCRIPTION OF THE FIGURES

The accompanying figures, which are incorporated herein and constitute part of this specification, are included to illustrate and provide a further understanding of the apparatus and system of the invention. Together with the description, the figures serve to explain the principles of the invention. In these figures.

DETAILED DESCRIPTION OF THE PREFERRED EMBODIMENTS

The purpose and advantages of the present invention will be set forth in and will become apparent from the description that follows, as well as will be learned by practice of the invention. Additional advantages of the invention will be realized and attained by the reactions particularly pointed out in the written description and claims hereof, as well as from the appended figures. To achieve these and other advantages and in accordance with the purpose of the invention, as embodied and described herein, the invention includes a convenient method of fluoromethylation of a fluoromethylatable substrate or compound. The invention also includes a convenient method of fluoromethylenation of a fluoromethylenatable substrate or compound. In particular, trifluoromethylation or difluoromethylenation are exemplified.

A fluoromethylatable substrate or compound is one that is capable of being fluoromethylated by a fluoromethylating agent. A "fluoromethylating agent" as the term is used herein refers to an agent capable of generating a fluoromethylating species that is capable of forming a bond with the fluoromethylatable substrate, according to the present process, while a fluoromethylenatable substrate or compound is one that is capable of being fluoromethylenated by a fluoromethylenating agent. The term "fluoromethylenating agent" as the term is used herein refers to an agent capable of generating a fluoromethylating species that is capable of forming two bonds with at least one fluoromethylenatable substrate, according to the present process. Suitable substrates or compounds include carbonyl compounds, disulfides and other electrophiles which undergo alkoxide or hydroxide induced nucleophilic fluoromethylation or fluoromethylenation.

Figure 1:
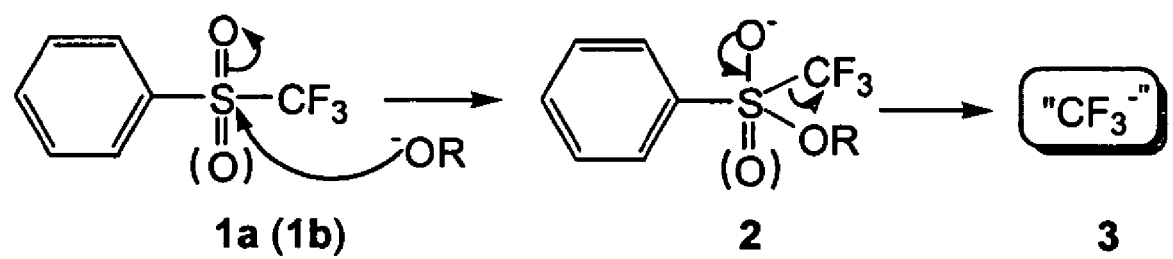
FIG. 1 is an illustration of certain reaction schemes that generate CF$_3$ species.

With reference to FIG. 1, a general reaction scheme that generates the $CF_3$ species is illustrated. As shown, a nucleophilic base, such as but not limited to an alkoxide or hydroxide, is utilized in the reaction and the carbon-sulfur bond of the trifluoromethylating agent, trifluoromethyl phenyl sulfone 1a or trifluoromethyl phenyl sulfoxide 1b, is cleaved to give a trifluoromethyl anion ($CF_3^-$) species. The trifluoromethyl anion undergoes addition to a substrate compound such as a carbonyl compound for trifluoromethylation of the substrate compound. Thus, a convenient and efficient trifluoromethylation process is provided. The driving force of this substitution is the formation of strong a S—O bond (348~551 kJ/mol) and the high polarity of the C—S bond of the trifluoromethylating agent, i.e., trifluoromethyl phenyl sulfone 1a or trifluoromethyl phenyl sulfoxide 1b. Notably, the generation of pseudohalide $CF_3^-$ species is somewhat similar to the reaction between benzenesulfonyl halides with alkoxides.

Figure 2:
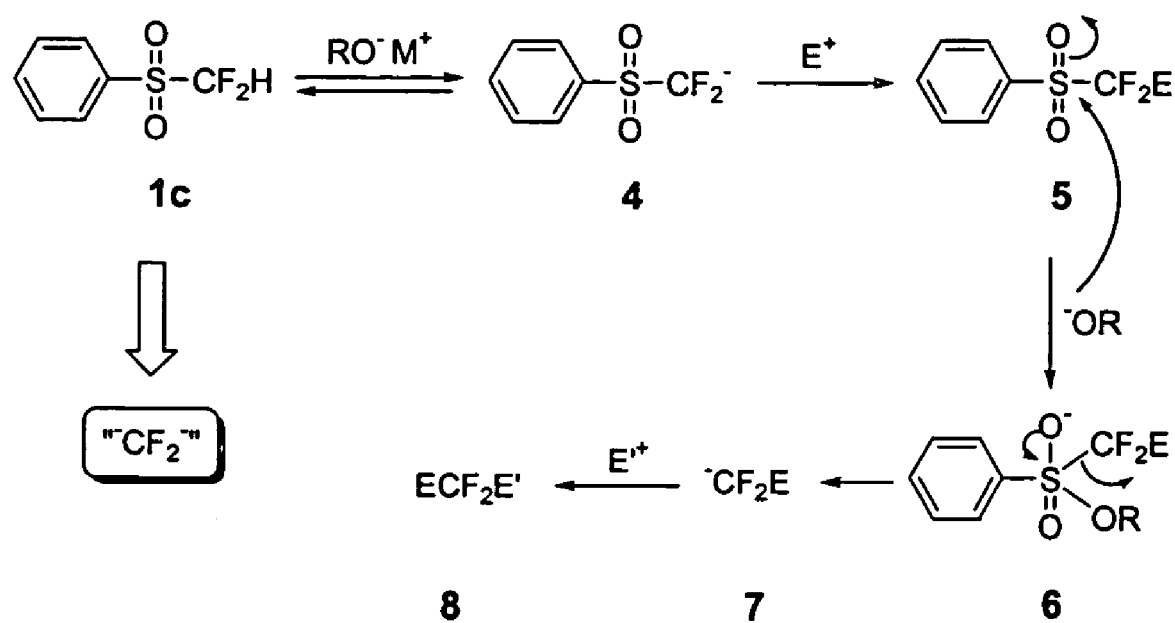
FIG. 2 is an illustration of certain reaction schemes that generate CF$_2$ species.

In another aspect of the invention, a substrate compound undergoes difluoromethylenation. In this aspect of the invention, the difluoromethylenating agent includes difluoromethyl phenyl sulfoxide, which acts as a "$^-CF_2^-$" synthon. Based on the previous mechanistic scheme to generate the $CF_3$ species as illustrated in FIG. 1, a similar type of S—C bond cleavage occurs with difluoromethyl phenyl sulfone 1c ($PhSO_2CF_2H$), as shown in FIG. 2.

The $CF_2H$ hydrogen of difluoromethyl phenyl sulfone 1c is rather acidic, and a common base such as sodium methoxide or even aqueous sodium hydroxide can deprotonate it in an equilibrium mode to generate $PhSO_2CF_2^-$ anion 4 as reported by Hine, J.; Porter, J. J. *J. Am. Chem. Soc.* 1960, 82, 6178–6181; Stahly, P. *J. Fluorine Chem.* 1989, 43, 53–66. Moreover, in 1989, Stahly had shown that the in situ generated anion 4 can react with aldehydes to give difluoromethylated carbinols in aqueous NaOH media in the presence of a phase-transfer agent (Stahly, P. *J. Fluorine Chem.* 1989, 43, 53–66). But Stahly did not report any S—C bond cleavage under the aqueous NaOH condition (at room temperature for 4 h). Obviously, aqueous NaOH is not nucleophilic enough to activate the S—C bond scission. Thus, indicative of these reports is that with the hydroxide or alkoxide base, the deprotonation on difluoromethyl sulfone 1c is much faster than the S—C bond cleavage. Advantageously, utilization of the alkoxide such as $^t$BuOK working both as a base and a nucleophile, the sulfone 1c reacts stepwise with two electrophiles to give new difluoromethylene-containing products, as illustrated in FIG. 2. Thus, difluoromethyl phenyl sulfone 1c acts as a selective difluoromethylene dianion ("$^-CF_2^-$") synthon.

Advantageously, both phenyl trifluoromethyl sulfone 1a and trifluoromethyl sulfoxide 1b are commercially available (b.p. 203° C./760 mmHg for 1a, b.p. 85~87° C./10 mmHg for 1b). Alternatively, both phenyl trifluoromethyl sulfone 1a and trifluoromethyl sulfoxide 1b and can also be conveniently prepared from trifluoromethane in high yields, as known in the art. Difluoromethyl phenyl sulfone 1c can also be readily prepared from chlorodifluoromethane, as known in the art. As these components of the present method are readily available or easily prepared, the present method of the invention provides a convenient route for efficient nucleophilic trifluoromethylation and difluoromethylenation of substrates.

Figure 3:
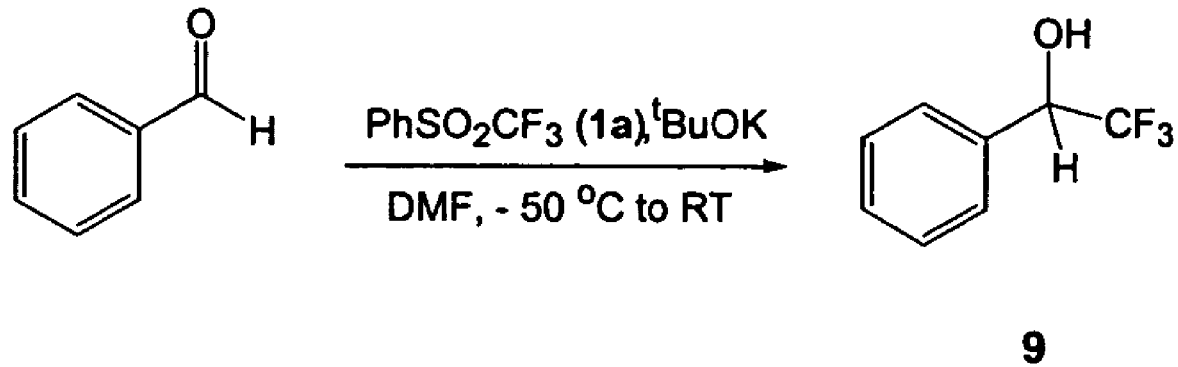
FIG. 3 is an illustration of a certain reaction scheme in which an alkoxide or hydroxide base attacks a trifluoromethylating agent to generate the trifluoromethyl anion.

Referring to FIG. 3, an alkoxide base, such as but not limited to potassium tert-butoxide ($^t$BuOK), is used as a nucleophile to attack the sulfur center of phenyl trifluoromethyl sulfone 1a and generates the trifluoromethyl anion. In one preferred embodiment, a DMF solution of $^t$BuOK (two molar equivalents) is slowly added into an equimolar mixture of phenyl trifluoromethyl sulfone 1a and benzaldehyde in DMF at –50° C. The reaction mixture is stirred at –50° C. for about 1 h, and then is warmed to room temperature over a period of about 2 h. The product is 1-phenyl-2-trifluoromethylethanol and is produced in about 71% yield.

Advantageously, only traces of benzoic acid and benzyl alcohol are detected by NMR in the reaction. Thus, the implication is that in the present invention at low temperature, the Cannizzaro reaction rate is much slower than the tert-butoxide induced trifluoromethylation process. Table 1 below shows the optimal reaction conditions. For example, as shown in Table 1, entry b, when excess benzaldehyde is introduced, the yield of the product 5 can be improved based on the amount of phenyl trifluoromethyl sulfone 1a used.

Shono and co-workers found that when they used $CF_3H/^t$BuOK/DMF to react with benzaldehyde at –50° C., benzyl alcohol and benzoic acid were formed by the competing Cannizzaro reaction (Shono, T.; Ishifume, M.; Okada, T.; Kashimura, S. *J. Org. Chem.* 1991, 56, 2). As mentioned above, the product of the present method is substantially free of benzyl alcohol and benzoic acid. Although Russell and Roques repeated the Shono reaction using excess $CF_3H$ (9.5 eq.) and $^t$BuOK (2.2 eq.) at –50° C., and 67% yield of trifluoromethylated product 5 was formed and no benzyl alcohol was detected (Russell, J.; Roques, N. *Tetrahedron* 1998, 54, 13771), they reported that the high reaction temperature with excess base could lead to Cannizzaro reaction and jeopardize the nucleophilic trifluoromethylation.

TABLE 1

Trifluoromethylation of Benzaldehyde by PhSO$_2$CF$_3$ Induced by Alkoxide or Hydroxide.

| | benzaldehyde | sulfone 1a | alkoxide | | solvent | temperature | time | yield (9, %) |
|---|---|---|---|---|---|---|---|---|
| a | 1 eq. | 1 eq. | t-BuOK | (2 eq.) | DMF | −50° C. | 1 h | 71 |
| b | 3 eq. | 1 eq. | t-BuOK | (2 eq.) | DMF | −30° C.~r.t. | 30 min | 91 |
| c | 1 eq. | 2 eq. | t-BuOK | (2 eq.) | DMF | −50° C.~r.t. | 3 h | 84 |
| d | 3 eq. | 1 eq. | MeONa | (3 eq.) | DMF | −30° C.~r.t. | 3 h | 30 |
| e | 3 eq. | 1 eq. | KOH | (8 eq.) | DMF | r.t. | 20 h | 45 |
| f | 3 eq. | 1 eq. | t-BuOK | (2 eq.) | DMSO | r.t. | 1 h | 76 |

[a]Yields were determined by $^{19}$F NMR based on the amount of 1a used.

In addition to $^t$BuOK being used as a nucleophilic base, other agents can be used such as sodium methoxide (CH$_3$ONa) and potassium hydroxide (KOH). (Table 1, entries d and e). Preferably, the nucleophilic base is potassium tert-butoxide. As can be seen from Table 1, sodium methoxide and potassium hydroxide had lower yields. Without being held to any theory, it is postulated that there are several possible reasons for the lower yields. First, both sodium methoxide and KOH can not readily dissolve in DMF, which can affect the reaction rate. Second, unlike potassium tert-butoxide, sodium methoxide may react with benzaldehyde via a Meerwein-Pondorff-Verley type reduction pathway. Third, KOH has lower nucleophilicity than $^t$BuOK, so the reaction rate can be slow. Here Cannizzaro reaction may still happen as a competing side-reaction, but it should not be a dominating factor to affect the yield since excess benzaldehyde is present.

Preferably, reaction takes place in a solvent. For purpose of illustration and not limitation the solvent can be DMF. As the CF$_3^-$/DMF adduct is not a necessary intermediate for this new type of nucleophilic trifluoromethylation, other solvents can be used such as (DMSO) dimethyl sulfoxide, as shown in Table 1, entry f. From a mechanistic point of view, however, it can be reasonably postulated that the intermediate species 2 shown in FIG. 1 is formed and could act as a trifluoromethylating agent.

As lower yields of product, after hydrolysis, is obtained when catalytic amounts of $^t$BuOK is used, excess amounts of $^t$BuOK (2 eq.) is preferred to achieve high yields in the trifluoromethylation reactions of the invention. Although catalytic amounts of $^t$BuOK have lower product yield, the introduction of additional $^t$BuOK increases product yield.

Advantageously, $^t$BuOK reacts with water readily and it may be partially hydrolyzed during storage and handling. Moreover, excess $^t$BuOK removes the moisture from the solvent and reagents. More importantly, excess $^t$BuOK in the reaction mixture eliminates the possibility of hydrolysis of CF$_3^-$ to form CF$_3$H. It is known that CF$_3$H can be deprotonated by $^t$BuOK and undergo trifluoromethylation of carbonyl compounds, thus, the present methodology allows the preparation of trifluoromethylated products in high yields in the case of non-enolizable aldehydes, as illustrated in Table 2, entries 1~5.

Advantageously, non-enolizable ketones can also be easily trifluoromethylated using the present invention, as illustrated in Table 2, entries 7~12. Since there is no Cannizarro reaction between ketones and $^t$BuOK, these reactions can be carried out even at higher temperatures, such as 25° C. Due to lower reactivity of ketones compared with aldehydes, the ketone reactions take a little bit longer time (2~3 h) to complete. However, with enolizable aldehydes and ketones, only low yield (10~30%) of trifluoromethylated products were observed, because of the competing and facile aldol reactions.

It is noteworthy that phenyl trifluoromethyl sulfoxide 1b worked equally well as 1a, the similar trifluoromethylations were observed with aldehyde and ketone (Table 2, entries 6 and 13).

TABLE 2

Reaction of Trifluoromethyl Phenyl Sulfone (1a) or Sulfoxide (1b) (2 equiv) with Non-enolizable Carbonyl Compounds (1 equiv) and $^t$BuOK (2.5 equiv) in DMF at −50° C. to Room Temperature.

| entry | carbonyl compound | trifluoromethylating agent | product | $^{19}$F NMR yield[a] (%) | (ppm)[b] |
|---|---|---|---|---|---|
| 1 | benzaldehyde (PhCHO) | 1a | PhCH(OH)CF$_3$ | 77 | −78.5 (d) |
| 2 | 2-naphthaldehyde | 1a | 2-naphthyl-CH(OH)CF$_3$ | 62 | −78.4 (d) |

TABLE 2-continued

Reaction of Trifluoromethyl Phenyl Sulfone (1a) or Sulfoxide (1b) (2 equiv) with
Non-enolizable Carbonyl Compounds (1 equiv) and ᵗBuOK (2.5 equiv) in DMF at −50° C.
to Room Temperature.

| entry | carbonyl compound | trifluoromethylating agent | product | yield[a] (%) | ¹⁹F NMR (ppm)[b] |
|---|---|---|---|---|---|
| 3 | 4-Et-C₆H₄-CHO | 1a | 4-Et-C₆H₄-CH(OH)CF₃ | 83 | −78.9(d) |
| 4 | 4-Ph-C₆H₄-CHO | 1a | 4-Ph-C₆H₄-CH(OH)CF₃ | 76 | −78.7(d) |
| 5 | ᵗBu-CHO | 1a | ᵗBu-CH(OH)CF₃ | 79[c] | −72.3(d) |
| 6 | PhCHO | 1b | Ph-CH(OH)CF₃ | 68 | −78.5(d) |
| 7 | Ph₂C=O | 1a | Ph₂C(OH)CF₃ | 86 | −74.5 |
| 8 | (4-Cl-C₆H₄)₂C=O | 1a | (4-Cl-C₆H₄)₂C(OH)CF₃ | 74 | −75.1 |
| 9 | 4-O₂N-C₆H₄-C(=O)-Ph | 1a | 4-O₂N-C₆H₄-C(OH)(CF₃)-Ph | 83 | −74.7 |
| 10 | 4-Me-C₆H₄-C(=O)-Ph | 1a | 4-Me-C₆H₄-C(OH)(CF₃)-Ph | 85 | −74.4 |
| 11 | 4-MeO-C₆H₄-C(=O)-Ph | 1a | 4-MeO-C₆H₄-C(OH)(CF₃)-Ph | 73 | −75.0 |

TABLE 2-continued

Reaction of Trifluoromethyl Phenyl Sulfone (1a) or Sulfoxide (1b) (2 equiv) with
Non-enolizable Carbonyl Compounds (1 equiv) and $^t$BuOK (2.5 equiv) in DMF at −50° C.
to Room Temperature.

| entry | carbonyl compound | trifluoromethylating agent | product | yield[a] (%) | $^{19}$F NMR (ppm)[b] |
|---|---|---|---|---|---|
| 12 | 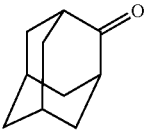 | 1a | 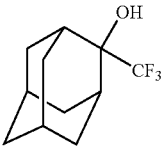 | 82 | −76.1 |
| 13 | 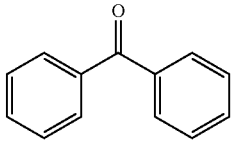 | 1b | 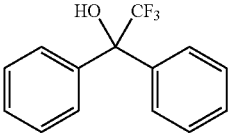 | 83 | −74.5 |

[a]Isolated yields.
[b]Use CFCl$_3$ as internal reference.
[c]Determined by $^{19}$F NMR using PhOCF$_3$ as internal standard.

Advantageously, the by-product of one of the preferred reactions is tert-butyl benzenesulfonate, which can be readily hydrolyzed into t-butyl alcohol and benzenesulfonic acid derivatives. Thus, aqueous washing can easily remove most of the by-products and simplify the purification process.

Figure 4:
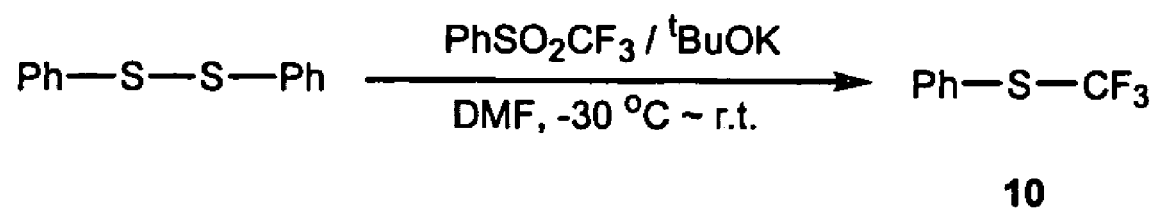
FIG. 4 is an illustration of a disulfide base undergoing trifluoromethylation.

With reference to FIG. 4, and as mentioned above, the substrate compound can be a disulfide. Disulfide substrates can easily be trifluoromethylated with the present invention. As shown in FIG. 3, PhSO$_2$CF$_3$ (1 eq.) and $^t$BuOK (2 eq.) reacted with diphenyl disulfide (1.2 eq.) at −30° C. to room temperature in 30 minutes to give quantitative conversion (87% isolated) of trifluoromethyl phenyl sulfide 10 ($^{19}$F NMR: −43.3 ppm). This reaction was even more facile than that of carbonyl compounds.

The trifluoromethyl phenyl sulfone/$^t$BuOK trifluoromethylation method can also be applied to other systems. For instance, methyl benzoate can be trifluoromethylated to generate 2,2,2-trifluoroacetophenone in 30% yield at about −50° C. to about −20° C. CF$_3$Cu can be in situ generated with trifluoromethyl phenyl sulfone/$^t$BuOK and copper iodide (CuI), and then further react with iodobenzene at 80° C. for 20 h to give α,α,α-trifluorotoluene in 26% yield.

Other types of sulfones, such as methyl trifluoromethyl sulfone (1d) can be used as the trifluoromethylating agent. When diphenyl disulfide was used as the model substrate, however, the reaction only gave minimal yield of product 7 (~2%). This is probably due to the facile deprotonation of the methyl group by $^t$BuOK, leading to other products.

Figure 5:
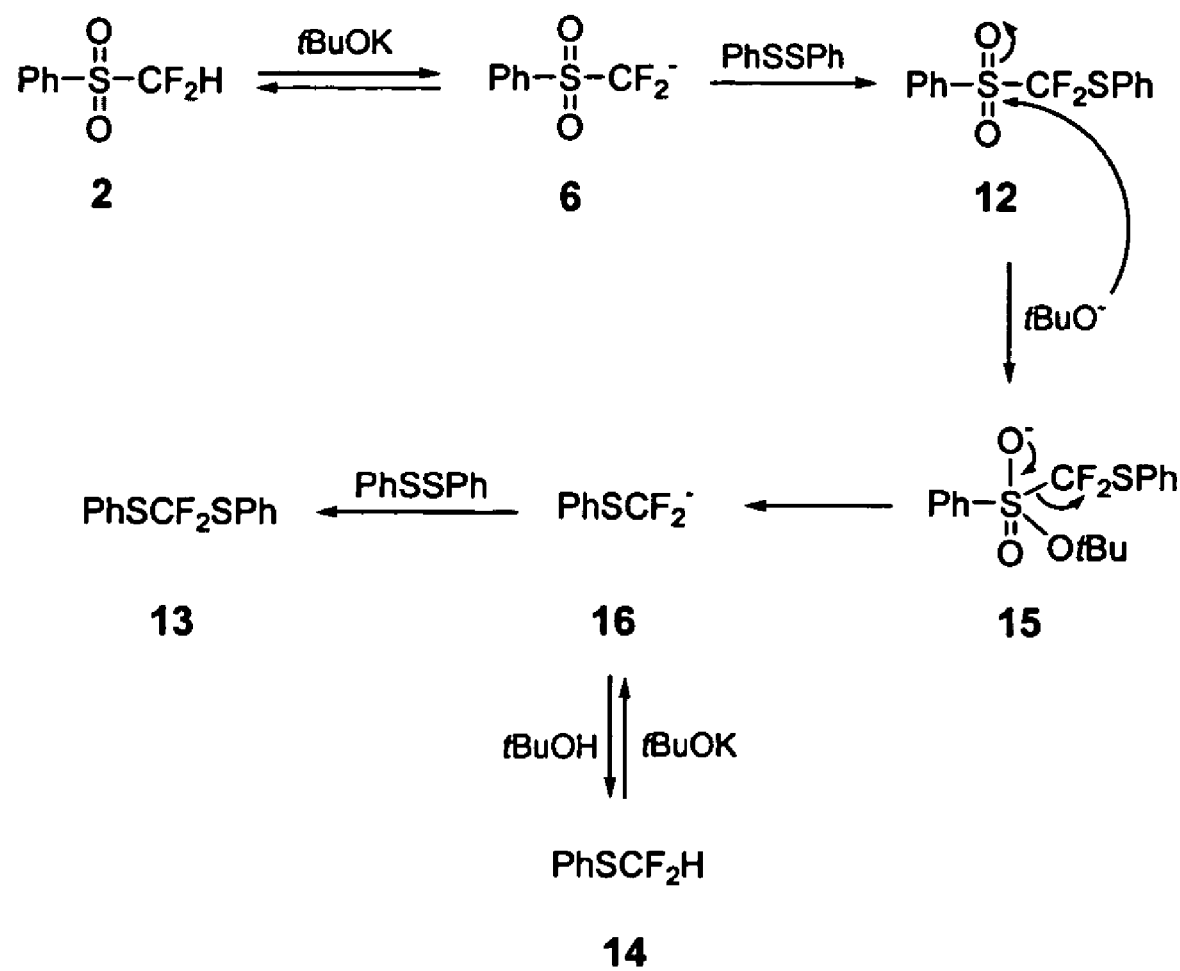
FIG. 5 illustrates a difluoromethylenation of a substrate generating mono-substituted and di-substituted products.

In another aspect of the invention, a method for preparing difluoromethylenated substrates is provided. In this aspect of the invention, a substrate is reacted with a difluoromethylenating agent and an alkoxide or an hydroxide base. The difluoromethylenating agent includes but is not limited to difluoromethyl phenyl sulfone or difluoromethyl phenyl sulfoxide. In particular and as shown in Table 3, and FIG. 5, a PhSO$_2$CF$_2$H/$^t$BuOK system is reacted with diphenyl disulfide (PhSSPh), as an electrophile. As shown in FIG. 5 and Table 3, entries b and g, with the different reactant ratio, both mono-substitution product 12 and double-substitution product 13 can be obtained at room temperature in high selectivity. Thus, the reactivities of deprotonation and S—C bond cleavage are different and these two steps can be controlled selectively, as illustrated in FIG. 5. Excess $^t$BuOK facilitates the completion of S—C bond cleavage process, which is similar to the above-mentioned trifluoromethyl sulfone system. Furthermore, the formation and consumption of PhSCF$_2$H 14 with time (Table 1, entries e and f) indicated that there is an equilibrium between anionic species 16 and 14 under the protonation/deprotonation with $^t$BuOH/$^t$BuOK.

TABLE 3

Difluoromethylenation of PhSSPh with 1c.

$$\underset{1c}{Ph-\overset{O}{\underset{\overset{\|}{O}}{S}}-CF_2H} + tBuOK + PhSSPh \xrightarrow{DMF}{RT}$$

$$\underset{12}{Ph-\overset{O}{\underset{\overset{\|}{O}}{S}}-CF_2SPh} + \underset{13}{PhSCF_2SPH} + \underset{14}{PhSCF_2H}$$

| | Reactant ratio | | | Reaction | Product yield[a] | | |
|---|---|---|---|---|---|---|---|
| Entry | 1c | tBuOK | 11 | time | 12 | 13 | 14 |
| a | 1 eq. | 1.0 eq. | 1.0 eq. | 30 min | 76% | 0% | 5% |
| b | 1 eq. | 1.5 eq. | 1.0 eq. | 50 min | 91% | 3% | 6% |
| c | 1 eq. | 2.5 eq. | 2.0 eq. | 14 h | 64% | 22% | 14% |
| d | 1 eq. | 3.0 eq. | 2.0 eq. | 4 h | 41% | 44% | 14% |
| e | 1 eq. | 3.5 eq. | 2.0 eq. | 4 h | 0% | 84% | 16% |
| f | 1 eq. | 3.5 eq. | 2.0 eq. | 15 h | 0% | 97% | 3% |
| g | 1 eq. | 4.0 eq. | 2.0 eq. | 4 h | 0% | 99% | 0% |

TABLE 3-continued

Difluoromethylenation of PhSSPh with 1c.

Ph—S(=O)(=O)—CF$_2$H + tBuOK + PhSSPh →(DMF/RT)

1c     11

Ph—S(=O)(=O)—CF$_2$SPh + PhSCF$_2$SPH + PhSCF$_2$H 12     13     14

| Entry | Reactant ratio | | Reaction | Product yield[a] | | |
|---|---|---|---|---|---|---|
| | 1c | tBuOK | 11 | time | 12 | 13 | 14 |

[a]The yields were determined by $^{19}$F NMR with PhOCF$_3$ as the internal standard.

Figure 6:
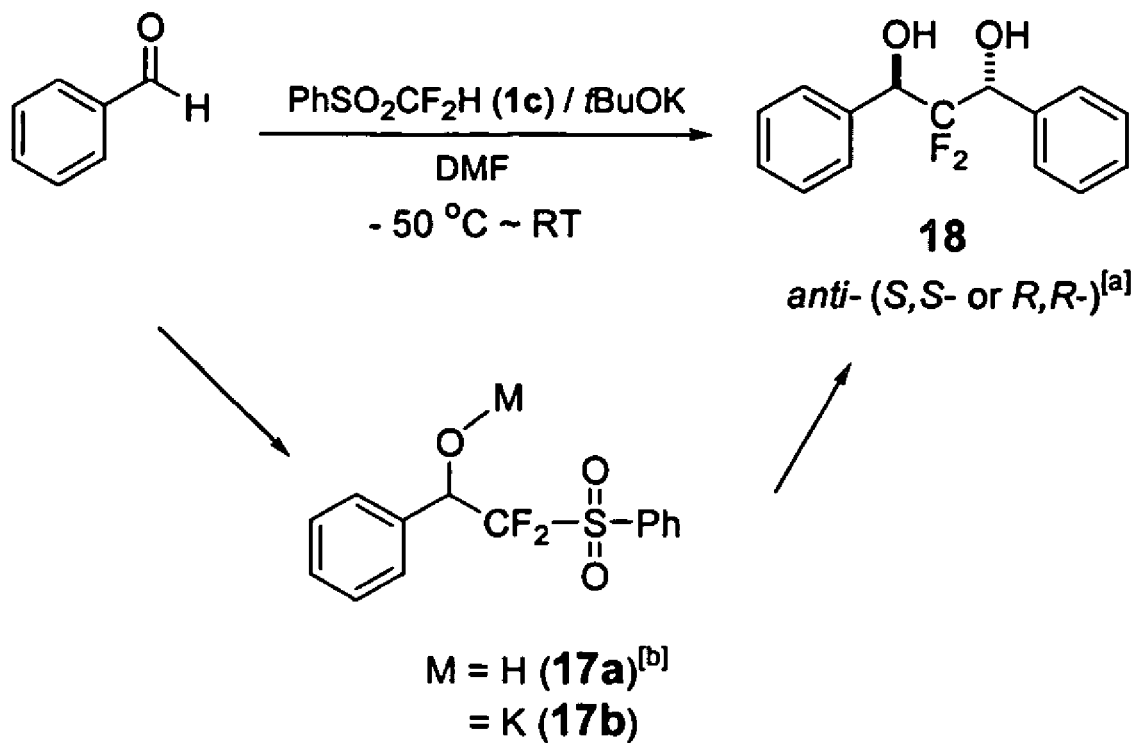
FIG. 6 is an illustration of a certain reaction scheme in which benzaldehyde reacts with trimethyl phenyl sulfone and tBuOK.
Figure 7:
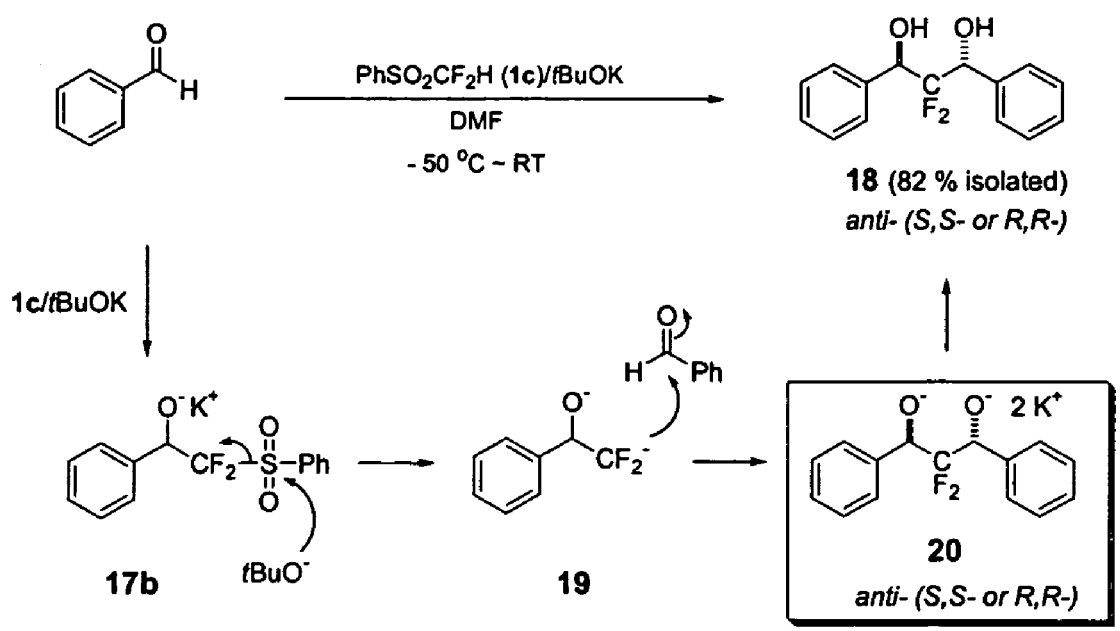
FIG. 7 illustrates the synthesis of a symmetrical anti-diol product.

Referring to FIG. 6, benzaldehyde is reacted with difluoromethyl phenyl sulfone/$^t$BuOK in DMF. Similar to the reaction with diphenyl disulfide, PhSO$_2$CF$_2$H (1.0 eq.)/$^t$BuOK (3.0 eq.) reacts with benzaldehyde (2.0 eq.) at −50° C.~RT for 90 minutes to generate mono-substituted product 17 (41% $^{19}$F NMR yield) as earlier shown by Stahly in the aqueous NaOH medium, and di-substituted product 18 (58% $^{19}$F NMR yield, anti/syn=98:1). When difluoromethyl phenyl sulfone (1.0 eq.)/$^t$BuOK (4.0 eq.) reacted with 3.0 eq. of PhCHO at −50° C. to RT for 8 h, under the activation of $^t$BuOK, the in situ formed alkoxide 17b undergoes S—C bond fission to generate a dianionic intermediate 19, which can further react with another molecule of benzaldehyde to form di-substituted anti-diol product 18a in excellent yield (92% $^{19}$F NMR yield, 82% isolated) and high diastereoselectivity (anti/syn=97:3, de=94%). The observed high diastereoselectivity can be interpreted by the charge-charge repulsion effect during the second addition, as shown in FIG. 7. To our knowledge, this may be the first example in which high diastereoselectivity has been achieved in a reaction where a dianionic species reacts with another neutral electrophile involving an intramolecular charge-charge repulsion effect (during the product formation) rather than the traditional steric control (based on the Cram's rule).

Table 4, below, demonstrates the application of this methodology to synthesize various 2,2-difluoropropan-1,3-diols with high stereoselectivity from non-enolizable aldehydes. The yield of diols is a little bit lower for electron-rich aldehydes (entries d and g), probably due to the relative instability of the corresponding dianion intermediate.

TABLE 4

Preparation of 2,2-difluoropropan-1,3-diols from aldehydes (3 equiv.) and difluoromethyl phenyl sulfone 1c (1 equiv.) with tBuOK (4 equiv.) in DMF at −50° C. to room temperature.

| Entry | Substrates | Products | Yield (%)[a] | anti-/syn- ratio[b] | de (%) |
|---|---|---|---|---|---|
| a | benzaldehyde | 1,3-diphenyl-2,2-difluoropropane-1,3-diol | 82 | 97:3 | 94 |
| b | 4-chlorobenzaldehyde | bis(4-chlorophenyl)-2,2-difluoropropane-1,3-diol | 78 | 94:6 | 88 |
| c | 4-bromobenzaldehyde | bis(4-bromophenyl)-2,2-difluoropropane-1,3-diol | 70 | 96:4 | 92 |
| d | 4-methoxybenzaldehyde | bis(4-methoxyphenyl)-2,2-difluoropropane-1,3-diol | 52 | 94:6 | 88 |

TABLE 4-continued

Preparation of 2,2-difluoropropan-1,3-diols from aldehydes (3 equiv.) and difluoromethyl phenyl sulfone 1c (1 equiv.) with tBuOK (4 equiv.) in DMF at −50° C. to room temperature.

| Entry | Substrates | Products | Yield (%)[a] | anti-lsyn-ratio[b] | de (%) |
|---|---|---|---|---|---|
| e | (2-naphthaldehyde) | (anti-diol from 2-naphthaldehyde) | 69 | 97:3 | 94 |
| f | (4-phenylbenzaldehyde) | (anti-diol from 4-phenylbenzaldehyde) | 75 | 96:4 | 92 |
| g | (furfural) | (anti-diol from furfural) | 63 | 93:7 | 86 |

[a]Isolated yields.
[b]anti-lsyn- ratio were determined by $^{19}$F NMR.

Figure 8:
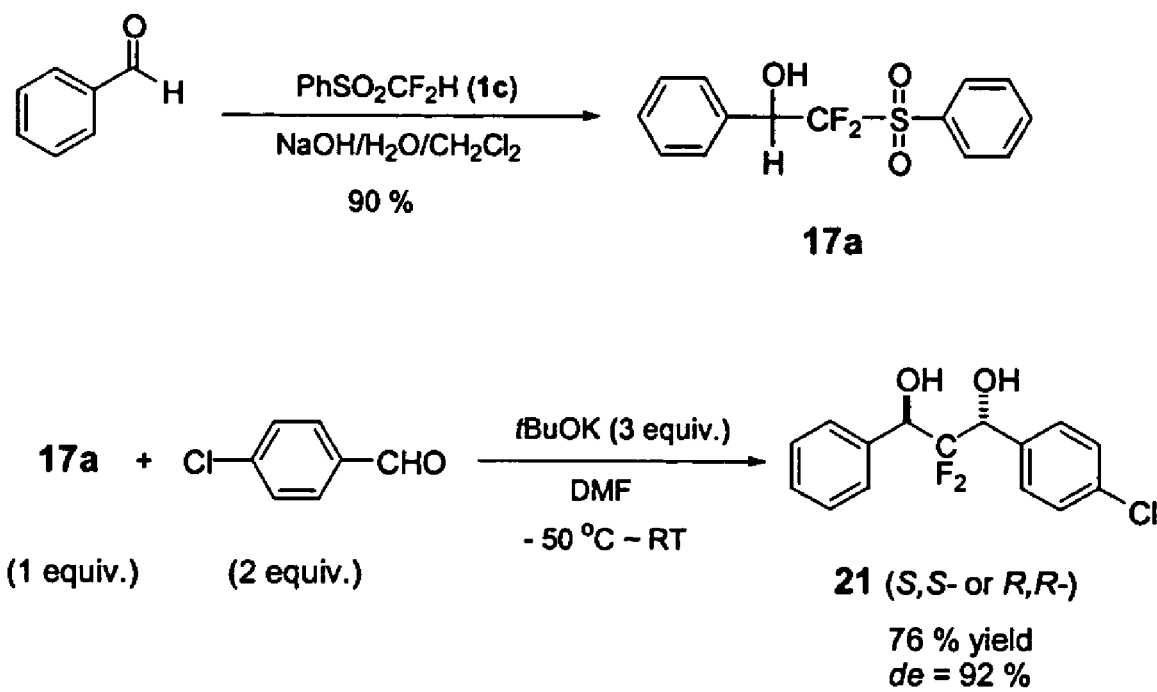
FIG. 8 illustrates the synthesis of a non-symmetric anti-diol product.

With reference to FIG. 8, in addition to the symmetric anti-2,2-difluoropropan-1,3-diols, this new methodology can also be used to synthesize non-symmetric anti-2,2-difluoropropan-1,3-diols. Difluoro(phenylsulfonyl)methyl substituted alcohol 17a can be easily obtained and isolated through Stahly's approach in high yield. The activation of 17a with $^t$BuOK generates the dianion intermediate 19, which further reacts with p-chlorobenzaldehyde to give non-symmetric anti-2,2-difluoropropan-1,3-diol 21 (after hydrolysis) with high diastereoselectivity.

The present invention will be further understood by the examples set forth below, which are provided for purpose of illustration and not limitation.

EXAMPLES

General: Unless otherwise mentioned, all other chemicals were purchased from commercial sources. Potassium tert-butoxide (95%) was used as received. DMF was distilled over calcium hydride, and stored over activated molecular sieve. Phenyl trifluoromethyl sulfone (1a) or trifluoromethyl phenyl sulfoxide (1b) was prepared by the oxidation of phenyl trifluoromethyl sulfide with hydrogen peroxide or mCPBA. Difluoromethyl phenyl sulfone (1c) was prepared using known procedures from chlorodifluoromethane and sodium thiophenoxide. Methyl trifluoromethyl sulfone (1d) was prepared using known procedures using methyl lithium and triflic anhydride. Most of the trifluorinated products are known, and their characterization results are consistent with the reported data.

$^1$H, $^{13}$C and $^{19}$F NMR spectra were recorded on superconducting NMR spectrometers at either 500 or 360 MHz. $^1$H NMR chemical shifts were determined relative to internal (CH$_3$)$_4$Si (TMS) at δ 0.0 or to the signal of a residual protonated solvent: CDCl$_3$ δ 7.26. $^{13}$C NMR chemical shifts were determined relative to internal TMS at δ 0.0 or to the $^{13}$C signal of solvent: CDCl$_3$ δ 77.0. $^{19}$F NMR chemical shifts were determined relative to internal CFCl$_3$ at δ 0.0. The $^{19}$F NMR yields were determined by the integration of the corresponding product peaks with respect to PhOCF$_3$ internal standard. The structures and ratios of anti- and syn-isomers of diols (3) were determined by $^{19}$F NMR (with the splitting patterns and the coupling constants) of the reaction products before isolation. Silica gel column chromatography was used to isolate the products using 60–200 mesh silica gel (from J. T. Baker). Mass spectra were recorded on GC-MS spectrometer with a mass selective detector at 70 eV. HRMS data were recorded on a VG 7070 high-resolution mass spectrometer.

Example 1

Preparation of 4-Methyl-α-phenyl-α-(trifluoromethyl)benzenemethanol

Into a dry Schlenk flask under an argon atmosphere, was added 7 mL DMF solution of phenyl trifluoromethyl sulfone (1a, 420 mg, 2 mmol) and 4-methylbenzophenone (196 mg, 1 mmol) at −50° C., was added 3 mL DMF solution of $^t$BuOK (280 mg, 2.5 mmol). The reaction flask was then sealed and the reaction mixture was then stirred from −50° C. for 1 h, followed by stirring at −50° C. to room temperature overnight. The reaction mixture was quenched with 10 mL of ice water, and extracted with ether (20 ml×3). The combined ether phase was washed with saturated NH$_4$Cl aqueous solution, followed by washing with water. After drying over MgSO$_4$, the ether solvent was removed under vacuum. The crude product was further purified by column chromatography (hexanes/ether=9/1) to give 225 mg of product, 4-methyl-α-phenyl-α-(trifluoromethyl)benzenemethanol as a colorless oily liquid, yield 85%. $^1$H NMR (CDCl$_3$): δ 2.36 (s, 3H); 2.89 (s, 1H); 7.17–7.51 (m, 9H). $^{19}$F NMR (CDCl$_3$): δ −74.4. MS: 266 (M$^+$).

Example 2

Preparation of 1-Phenyl-2,2,2-trifluoroethanol

The reaction condition is similar as described in Example 1 except that benzaldehyde was used as the substrate. Product 1-Phenyl-2,2,2-trifluoroethanol was isolated as a yellow oily liquid, 77% yield. $^1$H NMR (CDCl$_3$): δ 2.86 (s, 1H); 5.01 (q, $^3J_{H-F}$=6.3 Hz, 1H); 7.43 (m, 2H); 7.48 (m, 3H). $^{19}$F (CDCl$_3$): δ −78.5 (d, $^3J_{H-F}$=6.2 Hz). MS: 176 (M$^+$).

Example 3

Preparation of 1-(2'-Naphthyl)-2,2,2-trifluoroethanol

The reaction condition is similar as described in Example 1, except that 2-naphthaldehyde was used as the substrate. Product 1-(2'-naphthyl)-2,2,2-trifluoroethanol was isolated as a yellow solid, 62% yield. $^1$H NMR (CDCl$_3$): δ 2.76 (b, 1H); 5.19 (q, $^3J_{H-F}$=6.7 Hz, 1H); 7.51–7.96 (m, 7H). $^{19}$F (CDCl$_3$): δ −78.4 (d, $^3J_{H-F}$=6.7 Hz). MS: 226 (M$^+$).

Example 4

Preparation of 4'-Ethyl-phenyl-2,2,2-trifluoroethanol

The reaction condition is similar as described in Example 1, except that 4-ethylbenzaldehyde was used as the substrate. Product 4'-ethyl-phenyl-2,2,2-trifluoroethanol was isolated as a oily liquid, 83% yield. $^1$H NMR (CDCl$_3$): δ 1.25 (t, 3H); 2.60 (b, 1H); 2.67 (q, 2H); 4.99 (m, 1H); 7.25 (d, 2H); 7.38 (d, 2H). $^{19}$F NMR (CDCl$_3$): δ −78.9 (d, $^3J_{H-F}$=7.7 Hz). $^{13}$C NMR (CDCl$_3$): δ 15.4; 28.6; 72.6 (q, J=31.9 Hz); 124.3 (q, J=282.5 Hz); 127.4; 128.1; 131.2; 145.8. MS: 204 (M$^+$).

Example 5

Preparation of 4'-Biphenyl-2,2,2-trifluoroethanol

The reaction condition is similar as described in Example 1, except that 4-phenylbenzaldehyde was used as the substrate. Product 4'-biphenyl-2,2,2-trifluoroethanol was isolated as a white solid, 76% yield. $^1$H NMR (CDCl$_3$): δ 2.87 (b, 1H); 5.07 (m, 1H); 7.40–7.65 (m, 9H). $^{19}$F NMR (CDCl$_3$): δ −78.7 (d, J=7.6 Hz). $^{13}$C NMR (CDCl$_3$) δ 72.6 (q, J=31.6 Hz); 124.3 (q, J=281.8 Hz); 127.1; 127.3; 127.7; 127.8; 128.8; 132.8; 140.3; 142.5. MS: 252 (M$^+$).

Example 6

Preparation of α-Phenyl-α-(trifluoromethyl)benzenemethanol

The reaction condition is similar as described in Example 1, except that benzophenone was used as the substrate. Product α-phenyl-α-(trifluoromethyl)benzenemethanol was isolated as a oily liquid, 86% yield. $^1$H NMR (CDCl$_3$): δ 3.01 (b, 1H); 7.35–7.38 (m, 6H); 7.49–7.52 (m, 4H). $^{19}$F NMR (CDCl$_3$): δ −74.5. MS: 252 (M$^+$). For the same reaction, trifluoromethyl phenyl sulfoxide (PhSOCF$_3$) can also be used as the replacement of PhSO$_2$CF$_3$, the yield of the product α-Phenyl-α-(trifluoromethyl)benzenemethanol was 83%.

Example 7

Preparation of 4,4'-Dichloro-α-phenyl-α-(trifluoromethyl)benzenemethanol

The reaction condition is similar as described in Example 1, except that 4,4'-dichlorobenzophenone was used as the substrate. Product 4,4'-dichloro-α-phenyl-α-(trifluoromethyl)benzenemethanol was isolated as a pale yellow oily liquid, 74% yield. $^1$H NMR (CDCl$_3$): δ 2.95 (s, 1H); 7.34 (d, 4H); 7.40 (d, 4H). $^{19}$F NMR (CDCl$_3$): δ 75.1. MS: 320 (M$^+$).

Example 8

Preparation of 4-Nitro-α-phenyl-α-(trifluoromethyl)benzenemethanol

The reaction condition is similar as described in Example 1, except that 4-nitrobenzophenone was used as the substrate. Product 4-nitro-α-phenyl-α-(trifluoromethyl)benzenemethanol was isolated as a pale yellow oily liquid, 83% yield. $^1$H NMR (CDCl$_3$): δ 3.15 (s, 1H); 7.37–8.23 (m, 9H). $^{19}$F NMR (CDCl$_3$): δ −74.7. MS: 297 (M$^+$).

Example 9

Preparation of methoxy-α-phenyl-α-(trifluoromethyl)benzenemethanol

The reaction condition is similar as described in Example 1, except that 4-methoxybenzophenone was used as the substrate. Product 4-methoxy-α-phenyl-α-(trifluoromethyl)benzenemethanol was isolated as a oily liquid, 73% yield. $^1$H NMR (CDCl$_3$): δ 2.80 (s, 1H); 3.81 (s, 3H); 6.87–7.49 (m, 9H). $^{19}$F NMR (CDCl$_3$): δ −75.0. MS: 281 (M$^+$−1).

Example 10

Preparation of 2-(Trifluoromethyl)-2-adamantanol

The reaction condition is similar as described in Example 1, except that 2-adamantanone was used as the substrate. Product 2-(trifluoromethyl)-2-adamantanol was isolated as a white solid (sublimed), 82% yield. $^1$H NMR (CDCl$_3$): δ 1.56–2.27 (m, 15H). $^{19}$F (CDCl$_3$): δ −76.1. MS: 220 (M$^+$).

Example 11

Preparation of Phenyl Trifluoromethyl Sulfide

The reaction condition is similar as described in Example 1, except that PhSSPh was used as the substrate. phenyl trifluoromethyl sulfide, 87% yield, colorless liquid. $^1$H NMR (CDCl$_3$): δ 7.43 (t, J=7.5 Hz, 2H); 7.50 (t, J=7.5 Hz, 1H); 8.67 (d, J=7.5 Hz, 2H). $^{19}$F (CDCl$_3$): δ −43.2.

Example 12

Preparation of 2,2-difluoro-1,3-diphenyl-1,3-propanediol

The reaction was carried out in a Schlenk flask under an argon atmosphere. Into 5 mL DMF solution of difluoromethyl phenyl sulfone (1c, 480 mg, 2.5 mmol) and benzaldehyde (800 mg, 7.5 mmol) at −50° C., was added 5 mL DMF solution of $^t$BuOK (1.12 g, 10 mmol). The reaction flask was then sealed and the reaction mixture was then stirred from −50° C. for 1 h, followed by stirring at −50° C. to room temperature overnight. The reaction mixture was quenched with 20 mL of ice water, and extracted with ether (20 mL×3). The combined ether phase was washed with saturated NH$_4$Cl aqueous solution, followed by washing with water. After drying over MgSO$_4$, the ether solvent was removed under vacuum. The crude product was further purified by silica gel column (first hexanes/ethyl acetate (v/v=9:1); then hexanes/ethyl acetate (v/v=1:1)) to give 541 mg 2,2-Difluoro-1,3-diphenyl-1,3-propanediol as white crystalline solid, yield 82%, anti-/syn-ratio=97/3 determined by $^{19}$F NMR. For anti-isomer: $^1$H NMR (actone-d$_6$): δ 5.27 (m, 4H); 7.28–7.50 (m, 10H). $^{13}$C NMR (acetone-d$_6$): δ 72.3 (t, J=28.8 Hz); 121.6 (t, J=252.6 Hz); 128.5; 128.7; 129.0; 138.9. $^{19}$F NMR (acetone-d$_6$): δ −120.9 (pseudo t, J=11 Hz, 2F). For syn-isomer: $^{19}$F (acetone-d$_6$): δ −120.1 (dm, J=249.7 Hz); −125.0 (dt, J=249.8 Hz, 15.5 Hz). HRMS (DCI/NH$_3$) m/z calc'd for C$_{15}$H$_{18}$F$_2$NO$_2$ (M+NH4$^+$) 282.1305, found 282.1304.

Example 13

Preparation of 2,2-difluoro-1,3-bis(4'-chloro-phenyl)-1,3-propanediol

The reaction condition is similar as described in Example 12, except that 4-chlorobenzaldehyde was used as the substrate. Product 2,2-difluoro-1,3-bis(4'-chloro-phenyl)-1,3-propanediol was obtained as a pale yellow solid, 78% yield. For anti-isomer: $^1$H NMR (CDCl$_3$): δ 3.08 (d, J=4.9 Hz, 2H); 5.06 (td, J=11.3 Hz, 4.9 Hz, 2H); 7.37 (m, 8H). $^{13}$C NMR (CDCl$_3$): δ 73.00 (t, J=29.2 Hz); 118.75 (t, J=251.6 Hz); 128.59; 129.06; 134.29; 134.87. $^{19}$F NMR (CDCl$_3$): δ −119.222 (pseudo t, J=10.7 Hz). For syn-isomer: $^{19}$F NMR (CDCl$_3$): δ −119.35 (dt, J=256.5 Hz, 9.1 Hz); −127.67 (dt, J=256.5 Hz, 15.2 Hz). HRMS (EI): m/z calc'd for C$_{15}$H$_{12}$Cl$_2$F$_2$O$_2$ (M$^+$) 332.0182, found 332.0176.

Example 14

Preparation of 2,2-difluoro-1,3-bis(4'-bromo-phenyl)-1,3-propanediol

The reaction condition is similar as described in Example 12, except that 4-bromobenzaldehyde was used as the substrate. Product 2,2-difluoro-1,3-bis(4'-bromo-phenyl)-1,3-propanediol was obtained as a pale yellow solid, 70% yield. For anti-isomer: $^1$H NMR (CDCl$_3$): δ 3.20 (b, 2H); 5.02 (t, J=11.2 Hz, 2H); 7.30 (d, J=8.0 Hz, 4H); 7.51 (d, J=8.0 Hz, 4H). $^{13}$C NMR (CDCl$_3$): δ 73.05 (t, J=28.8 Hz); 118.67 (t, J=252.6 Hz); 123.09; 129.36; 131.53; 134.84. $^{19}$F NMR (CDCl$_3$): δ −119.14 (pseudo t, J=10.7 Hz). For syn-isomer: $^{19}$F NMR (CDCl$_3$): δ −118.96 (dt, J=254.8 Hz, 9.2 Hz); −127.48 (dt, J=254.8 Hz, 15.3 Hz). For anti-isomer: $^{19}$F NMR (CDCl$_3$): δ −119.1 (dt, J=254.8 Hz, 9.2 Hz); −127.5 (dt, J=254.8 Hz, 15.2 Hz). HRMS (EI): m/z calc'd for C$_{15}$H$_{12}$Br$_2$F$_2$O$_2$ (M$^+$) 421.9152, found 421.9156.

Example 15

Preparation of 2,2-difluoro-1,3-bis(4'-methoxy-phenyl)-1,3-propanediol

The reaction condition is similar as described in Example 12, except that 4-methoxybenzaldehyde was used as the substrate. Product 2,2-Difluoro-1,3-bis(4'-methoxy-phenyl)-1,3-propanediol was obtained as a pale yellow sticky liquid, 52% yield. For anti-isomer: $^1$H NMR (CDCl$_3$): δ 3.78 (s, 6H); 3.81 (b, 2H); 4.94 (t, J=11.8 Hz, 2H); 6.86 (d, J=8.5 Hz, 4H); 7.30 (d, J=8.4 Hz, 4H). $^{19}$F NMR (CDCl$_3$): δ −119.6 (pseudo t, J=13.1 Hz). $^{13}$C NMR (CDCl$_3$): δ 55.2; 73.1 (t, J=28.8 Hz); 113.62; 119.3 (t, J=251.3 Hz); 128.3; 129.0; 159.7. For Syn-isomer: $^{19}$F NMR (CDCl$_3$): δ −119.4 (dt, J=253.5 Hz, 9.2 Hz); −128.1 (dt, J=253.3 Hz, 15.1 Hz). HRMS (EI): m/z calc'd for C$_{15}$H$_{12}$Br$_2$F$_2$O$_2$ (M$^+$) 421.9152, found 421.9156.

Example 16

Preparation of 2,2-difluoro-1,3-bis(2'-naphthyl)-1,3-propanediol

The reaction condition is similar as described in Example 12, except that 2-naphthaldehyde was used as the substrate. Product 2,2-Difluoro-1,3-bis(2'-naphthyl)-1,3-propanediol was obtained as a pale yellow solid, 69% yield. For anti-isomer: $^1$H NMR (CDCl$_3$): δ 3.33 (b, 2H); 5.25 (t, J=11.3 Hz, 2H); 7.50~7.91 (m, 10H). $^{13}$C NMR (CDCl$_3$): δ 74.09 (t, J=28.9 Hz); 119.46 (t, J=251.7 Hz); 125.08; 126.30; 126.48; 127.34; 127.68; 128.10; 128.17; 132.97; 133.51. $^{19}$F NMR (CDCl$_3$): δ −118.35 (pseudo t, J=11.3 Hz). For syn-isomer: $^{19}$F NMR (CDCl$_3$): δ −117.7 (dm, J=250 Hz); −127.0 (dt, J=251 Hz, 15 Hz). HRMS (EI): m/z calc'd for C$_{23}$H$_{18}$F$_2$O$_2$ (M$^+$) 364.1275, found 364.1277.

Example 17

Preparation of 2,2-difluoro-1,3-bis(4'-biphenyl)-1,3-propanediol

The reaction condition is similar as described in Example 12, except that 4-phenylaldehyde used as the substrate. Product 2,2-Difluoro-1,3-bis(4'-biphenl)-1,3-propanediol was obtained as a pale yellow solid, 75% yield. For anti-isomer: $^1$H NMR: δ 3.48 (b, 2H); 5.17 (t, J=11.2 Hz, 2H); 7.36~7.60 (m, 18H). $^{13}$C NMR (CDCl$_3$): δ 73.54 (t, J=28.9 Hz); 119.32 (t, J=252.1 Hz); 127.06; 127.23; 127.67; 128.19; 130.01; 135.04; 140.53; 141.71. $^{19}$F NMR (CDCl$_3$): δ −119.04 (pseudo t, J=11.2 Hz). For syn-isomer: $^{19}$F NMR (CDCl$_3$): δ −119.3 (dm, J=251 Hz); −127.1 (dt, J=251 Hz, 15.1 Hz). HRMS (EI): m/z calc'd for C$_{27}$H$_{22}$F$_2$O$_2$ (M$^+$) 416.1588, found 416.1570.

Example 18

Preparation of 2,2-difluoro-1,3-bis(2'-furanyl)-1,3-propanediol

The reaction condition is similar as described in Example 12, except that 2-furanyl aldehyde phenylaldehyde used as the substrate. Product 2,2-difluoro-1,3-bis(2'-furanyl)-1,3-propanediol was obtained as a viscous liquid, 63% yield. For anti-isomer: $^1$H NMR (CDCl$_3$): δ 3.50 (b, 2H); 5.17 (t, J=11.0 Hz, 2H); 6.39 (m, 2H); 6.45 (mb, 2H); 743 (m, 2H). $^{13}$C NMR (CDCl$_3$): δ 67.38 (t, J=29.1 Hz); 109.80; 110.60; 18.84 (t, J=253.4 Hz); 143.13; 149.02. $^{19}$F NMR (CDCl$_3$): δ −120.95 (pseudo t, J=11.0 Hz). For syn-isomer: $^{19}$F NMR (CDCl$_3$): δ −120.5 (dm, J=253 Hz); −125.3 (dt, J=253 Hz, 14 Hz). HRMS (EI): m/z calc'd for C$_{11}$H$_{10}$F$_2$O$_4$ (M$^+$) 244.0547, found 244.0550.

Example 19

Preparation of 2,2-Difluoro-1-phenyl-3-(4'-chlorophenyl)-1,3-propanediol

Into the mixture of $PhSO_2CF_2CH(OH)Ph$ (120 mg, 0.4 mmol) and 4-chlorobenzaldehyde (113 mg, 0.8 mmol) in DMF (3 mL) at –50° C., was added t-BuOK (90 mg, 0.8 mmol) in 2 mL DMF. The reaction mixture was stirred at –50° C. to RT overnight. The reaction was then quenched with cold NaCl aqueous solution, followed by extraction with $Et_2O$ (20 mL×3). After drying over $MgSO_4$ and solvent removal, the product 2,2-Difluoro-1-phenyl-3-(4'-chlorophenyl)-1,3-propanediol was obtained by chromatography as a white solid, 76% yield. For anti-isomer: $^1H$ NMR ($CDCl_3$): δ 3.22 (m, 2H); 5.04 (td, J=11.0 Hz, 2H); 7.36 (m, 9H). $^{13}C$ NMR ($CDCl_3$): δ 72.9 (t, J=29 Hz); 73.8 (t, J=29 Hz); 118.7 (t, J=259 Hz); 127.6; 128.6; 129.0; 134.3; 134.8. $^{19}F$ NMR($CDCl_3$): δ –118.2~120.1 (m).

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. A method for preparing a fluoromethylated substrate, which comprises reacting a fluoromethylatable substrate with a fluorormethylating agent comprising a trifluoromethylated sulfone or sulfoxide compound and in the presence of an alkoxide or hydroxide base under conditions sufficient to trifluoromethylate the substrate; wherein the fluoromethylatable substrate comprises a compound selected from the group consisting of carbonyl compounds, disulfide compounds, methyl benzoate, aldehydes and ketones.

2. The method of claim 1, wherein the reaction conditions include a temperature between about –25° C. to about 55° C. and a time of between 30 minutes to 20 hours.

3. The method of claim 1 which further comprises adding the base to a mixture that includes the substrate and the fluoromethylating agent to form a reaction mixture, stirring the reaction mixture at about –50° C. to about –30° C., and warming the reaction mixture to about room temperature.

4. The method of claim 3, wherein the reaction mixture is warmed for about 2 hours.

5. The method of claim 1, wherein the ketone or carbonyl compound is a non-enolizable compound.

6. The method of claim 1, wherein the substrate comprises beozaldehyde, 2-naphthaldehyde, 4-ethylbenzaldehyde, 4-phenylbenzaldehyde, 2,2-dimethyl propanaldehyde, benzophenone, 4'4'dichlorobenzophenone, 4-nitrobenzophenone, 4-methoxybenzophenone, 4-methylbenzophenone, 2-adamantanone, or diphenyl disulfide.

7. The method of claim 1, wherein the base is potassium tert-butoxide, sodium methoxide, or potassium hydroxide.

8. The method of claim 1, wherein the fluoromethylating agent is trifluoromethyl phenyl sulfone, trifluoromethyl phenyl sulfoxide, or methyl trifluoromethyl sulfone.

9. The method of claim 1, wherein the fluoromethylated substrate is 4-methyl-αphenyl-α-(triflouromethyl)bezenemethanol, 1-phenyl-2,2,2-trifluoroethanol, 1-(2'-naphthyl)-2,2,2-trifluoroethanol, 4'-ethyl-phenyl-2,2,2-trifluoroethanal, 4'-biphenyl-2,2,2-trifluoroethanol, α-phenyl-α-(trifluoromethyl)benzenemethanol, 4,4'-dichloro-α-phenyl-α-(trifluoromethyl)benzenemethanol, 4-nitro-phenyl-α-(trifluoromethyl)benzenemethanol, methoxy-α-phenyl-α-(trifluoromethyl)benzenemethanol, 2-(trifluoromethyl)-2-adamantanol, 2-(trifluoromethyl)-2-adamantanol, or phenyl trifluoromethyl sulfide.

10. The method of claim 9, wherein the fluoromethylated substrate is substantially lacking in Cannizzaro products of aromatic aldehydes.

11. The method of claim 1, wherein the reaction is carried out in the presence of a solvent.

12. The method of claim 11, wherein the solvent is DMF or DMSO.

13. A method for preparing a fluoromethylenated substrate, which comprises reacting a fluoromethylenatable substrate with a fluoromethylenating agent and in the presence of an alkoxide or hydroxide base under conditions sufficient to fluoromethylenate the substrate, wherein the fluoromethylenating agent generates a fluoromethylenating species which forms two bonds with at least one substrate; wherein the fluoromethylatable substrate comprises a compound selected from group consisting of carbonyl compounds, disulfide compounds, methyl benzoate, aldehydes and ketones.

14. The method of claim 13, wherein the fluoromethylenating agent is a difluoromethylenating compound so that the substrate is difluoromethylenated.

15. The method of claim 14, wherein the difluoromethylenating agent is difluoromethyl phenyl sulfone or difluoromethyl sulfoxide.

16. The method of claim 14, wherein the substrate comprises benzaldehyde, 4-chlorobenzaldehyde, 4-bromobenzaldehyde, 4-methoxybenzaldehyde, 2-naphthaldehyde 4-phenylbenzaldehyde, 2-furanyl aldehyde, or diphenyl disulfide.

17. The method of claim 14, wherein the difluoromethylenated substrate is 2,2-difluoro-1,3-diphenyl-1,3-propanediol 2,2difluoro-1,3-bis(4'-chloro-phenyl) -1,3-propanediol, 2,2-difluoro-3,1-bis(4'-bromo-phenyl)-1,3-propanediol, 2,2-difluoro-1,3-bis(4'-methoxy-phenyl)-1,3-propanediol, 2,2-difluoro-1,3-bis(2'-naphthyl)1,3-propanediol, 2,2-difluoro-1,3-bis(4'-biphenyl)-1,3-propanediol, 2,2-difluoro-1,3-bis(2'-furanyl) -1,3-propanediol, or 2,2difluoro-1-phenyl-3-(4'-chlorophenyl)-1,3-propanediol.

18. The method of claim 17, wherein the difluoromethylenated substrate is 2,2-difluoro-propan-1,3-diol, and further wherein the diol is non-symmetric.

19. The method of claim 14, wherein the difluoromethylenated substrate is a difluoromethyldisulfide having the general formula $RSCF_2SR$, wherein R is an aryl, or an alkyl group.

20. The method of claim 13, wherein the reaction conditions include a temperature between about –25° C. to about 550° C. and a time of between 30 minutes to 20 hours.

21. The method of claim 13, which further comprises adding the base to a mixture that includes the substrate and the fluoromethylenating agent to form a reaction mixture, stirring the reaction mixture at about –50° C. to about –30° C., and warming the reaction mixture to about room temperature.

22. The method of claim 21, wherein the reaction mixture is warmed for about 2 hours.

23. The method of claim 13, wherein the ketone or carbonyl compound is a non-enolizable compound.

24. The method of claim 13, wherein the base is potassium tert-butoxide, sodium methoxide, or potassium hydroxide.

25. The method of claim 13, wherein the reaction is carried our in the presence of a solvent.

26. The method of claim 25, wherein the solvent is DMF or DMSO.

* * * * *

UNITED STATES PATENT AND TRADEMARK OFFICE
CERTIFICATE OF CORRECTION

PATENT NO. : 7,087,789 B2
APPLICATION NO. : 10/755902
DATED : August 8, 2006
INVENTOR(S) : Prakash et al.

It is certified that error appears in the above-identified patent and that said Letters Patent is hereby corrected as shown below:

Column 21:
Line 29 (claim 1, line 3), change "fluorormethylating" to -- fluoromethylating --.
Line 48 (claim 6, line 2), change "beozaldehyde" to -- benzaldehyde --.
Line 50 (claim 6, line 4), change "4'4'dichlorobenzophenone" to
-- 4'4'-dichlorobenzophenone --.
Line 58 (claim 9, line 2), change "4-methyl-αphenyl-α-(triflouromethyl)bezen-" to
-- 4-methyl-α-phenyl-α-(trifluoromethyl)benzen- --.
Line 61 (claim 9, line 5), change "nal," to -- nol, --.

Column 22:
Line 15 (claim 13, line 9), after "pound selected from" insert -- the --.
Line 26 (claim 16, line 3), change "2-naphthaldehyde" to -- 2-naphthaldehyde, --.
Line 31 (claim 17, line 3), change "panediol 2,2difluoro-1,3-bis(4'-chloro-phenyl)" to
-- panediol, 2,2-difluoro-1,3-bis(4'-chloro-phenyl) --
Line 32 (claim 17, line 4), change "2,2-difluoro-3,1-bis(4'-bromo-phenyl)-1,3-" to
-- 2,2-difluoro-1,3-bis(4'-bromo-phenyl)-1,3- --.
Line 37 (claim 17, line 9), change "2,2difluoro-1-phenyl-3-(4'-chlorophenyl)-l," to
-- 2,2-difluoro-1-phenyl-3-(4'-chlorophenyl)-l, --.
Line 48 (claim 20, line 3), change "550°C." to --55°C.--.
Line 63 (claim 25, line 2), after "carried" change "our" to -- out --.

Signed and Sealed this

Fifth Day of December, 2006

JON W. DUDAS
*Director of the United States Patent and Trademark Office*